(12) United States Patent
Schulte et al.

(10) Patent No.: US 7,405,261 B2
(45) Date of Patent: Jul. 29, 2008

(54) ORGANOMETALLIC TRANSITION METAL COMPOUND, BISCYCLOPENTADIENYL LIGAND SYSTEM, CATALYST SYSTEM AND PROCESS FOR PREPARING POLYOLEFINS

(75) Inventors: Jörg Schulte, Frankfurt (DE); Jörg Schottek, Frankfurt (DE); Yoshikuni Okumura, Kanagawa (JP)

(73) Assignee: Basell Polyolefine GmbH, Wesseling (DE)

( * ) Notice: Subject to any disclaimer, the term of this patent is extended or adjusted under 35 U.S.C. 154(b) by 193 days.

(21) Appl. No.: 10/537,677

(22) PCT Filed: Dec. 2, 2003

(86) PCT No.: PCT/EP03/13553

§ 371 (c)(1), (2), (4) Date: Jun. 6, 2005

(87) PCT Pub. No.: WO2004/052945

PCT Pub. Date: Jun. 24, 2004

(65) Prior Publication Data

US 2006/0122345 A1 Jun. 8, 2006

Related U.S. Application Data

(60) Provisional application No. 60/444,595, filed on Feb. 3, 2003.

(30) Foreign Application Priority Data

Dec. 6, 2002 (DE) ................. 102 57 332

(51) Int. Cl.
C08F 4/76 (2006.01)
C07F 17/00 (2006.01)
(52) U.S. Cl. ............. 526/170; 526/160; 526/943; 526/941; 556/53; 502/103
(58) Field of Classification Search ............ 556/53; 526/160, 170, 943
See application file for complete search history.

(56) References Cited

U.S. PATENT DOCUMENTS

| | | | |
|---|---|---|---|
| 5,770,753 A | 6/1998 | Küber et al. | |
| 5,786,432 A | 7/1998 | Küber et al. | |
| 5,840,644 A | 11/1998 | Küber et al. | |
| 5,840,947 A * | 11/1998 | Kuber et al. | 556/8 |
| 6,051,727 A | 4/2000 | Küber et al. | |
| 6,242,544 B1 | 6/2001 | Küber et al. | |
| 6,255,506 B1 | 7/2001 | Küber et al. | |
| 6,417,302 B1 | 7/2002 | Bohnen | |
| 6,444,606 B1 | 9/2002 | Bingel et al. | |
| 6,482,902 B1 | 11/2002 | Bohnen et al. | |
| 6,492,539 B1 * | 12/2002 | Bingel et al. | 556/11 |
| 6,589,905 B1 | 7/2003 | Fischer et al. | |
| 6,686,055 B2 * | 2/2004 | Tanaka et al. | 428/516 |
| 6,784,305 B2 | 8/2004 | Schulte et al. | |
| 7,199,274 B2 | 4/2007 | Schulte et al. | |
| 2001/0021755 A1 | 9/2001 | Küber et al. | |
| 2003/0009046 A1 | 1/2003 | Bingel et al. | |
| 2003/0199703 A1 * | 10/2003 | Schulte et al. | 556/53 |

FOREIGN PATENT DOCUMENTS

| | | |
|---|---|---|
| EP | 0 576 970 | 1/1994 |
| EP | 0 629 631 | 12/1994 |
| EP | 0 743 317 | 11/1996 |
| WO | WO-91/09882 | 7/1991 |
| WO | WO-96/00243 | 1/1996 |
| WO | WO-98/40419 | 9/1998 |
| WO | WO-99/06414 | 2/1999 |
| WO | WO-99/40129 | 8/1999 |
| WO | WO-00/05277 | 2/2000 |
| WO | WO-00/31090 | 6/2000 |
| WO | WO-02/18397 | 3/2002 |
| WO | 2004/037756 | 5/2004 |

OTHER PUBLICATIONS

Rheingold, A. L. et al., "Preparation and Properties of Chiral Titanocene and Zirconocene dichloride Complexes of a Chiral Ligand", Organometallics (1992), 11, pp. 1869-1876.

* cited by examiner

Primary Examiner—Rip A. Lee
(74) Attorney, Agent, or Firm—William R. Reid

(57) ABSTRACT

The present invention relates to compounds of the formula (I):

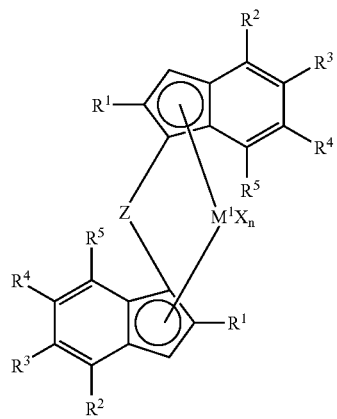

where
$M^1$ is an element of group 3, 4, 5 or 6 of the Periodic Table,
X are halogen, hydrogen, $C_1$-$C_{20}$-alkyl, $C_2$-$C_{20}$-alkenyl, $C_6$-$C_{22}$-aryl, alkylaryl or arylalkyl,
n is a natural number from 1 to 4.
$R^1$ is hydrogen or a $C_1$-$C_{40}$ radical,
$R^2$ is a substituted or unsubstituted $C_6$-$C_{40}$-aryl radical or $C_2$-$C_{40}$-heteroaromatic radical containing at least one heteroatom,
$R^3$ is hydrogen or a $C_1$-$C_{40}$ radical, or the radicals $R^2$ and $R^3$ together form a ring system,
$R^4$ is hydrogen or a $C_1$-$C_{40}$ radical,
$R^5$ is a $C_1$-$C_{40}$ radical, and
Z is a divalent group $CR^8R^9$—$CR^{10}R^{11}$, where $R^8$, $R^9$, $R^{10}$ and $R^{11}$ are hydrogen or a $C_1$-$C_{40}$ radical.

9 Claims, No Drawings

ORGANOMETALLIC TRANSITION METAL COMPOUND, BISCYCLOPENTADIENYL LIGAND SYSTEM, CATALYST SYSTEM AND PROCESS FOR PREPARING POLYOLEFINS

RELATED APPLICATIONS

This application is a national stage application (under 35 U.S.C. 371) of PCT/EP2003/013553 filed Dec. 2, 2003 which claims benefit to German application 102 57 332.8 filed Dec. 6, 2002 and U.S. provisional application 60/444,595 filed Feb. 3, 2003.

The present invention relates to organometallic transition metal compounds of the formula (I)

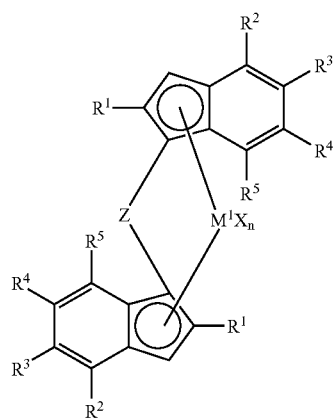

(I)

where
- $M^1$ is an element of group 3, 4, 5 or 6 of the Periodic Table of the Elements or the lanthanides,
- X are identical or different and are each halogen, hydrogen, $C_1$-$C_{20}$-alkyl, $C_2$-$C_{20}$-alkenyl, $C_6$-$C_{22}$-aryl, alkylaryl or arylalkyl each having from 1 to 10 carbon atoms in the alkyl part and from 6 to 22 carbon atoms in the aryl part, —$OR^6$ or —$NR^6R^7$, where two radicals X may also be joined to one another,
- n is a natural number from 1 to 4 which corresponds to the oxidation number of $M^1$ minus 2,
- $R^1$ is hydrogen or a $C_1$-$C_{40}$ radical,
- $R^2$ is a substituted or unsubstituted $C_6$-$C_{40}$-aryl radical or $C_2$-$C_4$-heteroaromatic radical containing at least one heteroatom selected from the group consisting of O, N, S and P,
- $R^3$ is hydrogen or a $C_1$-$C_{40}$ radical,
- or the radicals $R^2$ and $R^3$ together form a ring system,
- $R^4$ is hydrogen or a $C_1$-$C_{40}$ radical,
- $R^6$ is a $C_1$-$C_{40}$ radical, and
- Z is a divalent group $CR^8R^9$—$CR^{10}R^{11}$, where $R^8$, $R^9$, $R^{10}$ and $R^{11}$ are identical or different and are each hydrogen or a $C_1$-$C_{40}$ radical.

The present invention further relates to biscyclopentadienyl ligand systems having such a substitution pattern, catalyst systems comprising at least one of the organometallic transition metal compounds of the present invention, a process for preparing polyolefins by polymerization or copolymerization of at least one olefin in the presence of one of the catalyst systems of the present invention and the use of the biscyclopentadienyl ligand systems of the present invention for preparing organometallic transition metal compounds.

Research and development on the use of organometallic transition metal compounds, in particular metallocenes, as catalyst components for the polymerization and copolymerization of olefins with the aim of preparing tailored polyolefins has been carried out intensively in universities and in industry during the past 15 years.

Now, both polyolefins based on ethylene and prepared by means of metallocene catalyst systems and, in particular, polyolefins based on propylene and prepared by means of metallocene catalyst systems represent a dynamically growing market segment.

Variation of the substitution pattern on the ligand systems of ansa-metallocenes alters the steric circumstances around the active center and also its electronic structure. This makes it possible to influence, for example, the polymerization behavior of the catalyst constituents and also finally the properties of the polymers, e.g. isotacticity, chain length or molar mass and also the macroscopic materials properties of these polymers.

In the polymerization of olefins, in particular propylene, the catalyst system which usually comprises at least one organometallic transition metal compound and a cocatalyst component such as an aluminoxane, a strong Lewis acid or an ionic compound is generally used in supported form in order to avoid formation of deposits in the reactor.

EP 0 629 631 describes $C_2$-symmetric 2,4,7-substituted ansa-metallocenes. It is demonstrated that the melting point of polypropylene prepared by means of such metallocenes is reduced compared to polypropylene which has been prepared using a corresponding $C_2$-symmetrically 2,4-substituted ansa-metallocene. A significant influence of the substituents in the 7 position on the molecular weight of the polypropylenes was not observed.

WO 02/18397 describes an effective process for preparing highly substituted alkyl-bridged metallocenes. However, the catalysts prepared using the metallocenes mentioned there give polypropylenes which do not have sufficiently high melting points. It is an object of the present invention to find alkyl-bridged metallocenes which, when used as constituents of supported catalyst systems, are able to produce polypropylenes having a melting point higher than that of polypropylenes produced using known alkyl-bridged metallocenes. In addition, for economic reasons, the activity of the metallocenes to be discovered should not be inferior to that of the known metallocenes.

We have found that this object is achieved by the organometallic transition metal compounds of the formula (I) mentioned at the outset.

$M^1$ is an element of group 3, 4, 5 or 6 of the Periodic Table of the Elements or the lanthanides, for example titanium, zirconium, hafnium, vanadium, niobium, tantalum, chromium, molybdenum or tungsten, preferably titanium, zirconium, hafnium, particularly preferably zirconium and hafnium, and very particularly preferably zirconium.

The radicals X are identical or different, preferably identical, and are each halogen, for example fluorine, chlorine, bromine, iodine, preferably chlorine, hydrogen, $C_1$-$C_{20}$-, preferably $C_1$-$C_4$-alkyl, $C_2$-$C_{20}$-, preferably $C_2$-$C_4$-alkenyl, $C_6$-$C_{22}$-, preferably $C_6$-$C_{10}$-aryl, an alkylaryl or arylalkyl group having from 1 to 10, preferably from 1 to 4, carbon atoms in the alkyl part and from 6 to 22, preferably from 6 to 10, carbon atoms in the aryl part, —$OR^6$ or —$NR^6R^7$, preferably —$OR^6$, where two radicals X may also be joined to one another, preferably two radicals —$OR^6$ which form, in particular, a substituted or unsubstituted 1,1'-di-2-phenoxide radical. Two radicals X can also form a substituted or unsubstituted diene ligand, in particular a 1,3-diene ligand. The radicals $R^6$ and $R^7$ are each $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 22, preferably from 6 to 10, carbon atoms in the aryl radical.

The index n is a natural number from 1 to 4 which corresponds to the oxidation number of $M^1$ minus 2, and is preferably 2 for the elements of group 4 of the Periodic Table of the Elements.

The radical $R^1$ is hydrogen or a $C_1$-$C_{40}$ radical. $R^1$ is preferably a cyclic, branched or unbranched $C_1$-$C_{20}$-, preferably $C_1$-$C_8$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part or a $C_2$-$C_{40}$-, preferably $C_4$-$C_{24}$ heteroaromatic radical, particularly selected from the group consisting of substituted or unsubstituted thienyl radicals or of substituted or unsubstituted furyl radicals. Examples of particularly preferred radicals $R^1$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, 2-(5-methyl)thienyl, 2-(5-methyl)furyl, benzyl and 2-phenylethyl, in particular methyl, ethyl or isopropyl.

The radical $R^2$ is a substituted or unsubstituted $C_6$-$C_{40}$-aryl radical or $C_2$-$C_{40}$-heteroaromatic radical containing at least one heteroatom selected from the group consisting of O, N, S and P. The radical $R^2$ is preferably an unsubstituted or alkyl-substituted $C_6$-$C_{40}$-aryl radical having from 1 to 10, preferably from 1 to 4, carbon atoms in the alkyl part and from 6 to 22, preferably from 6 to 10, carbon atoms in the aryl part, with the radicals also being able to be halogenated. Examples of preferred radicals $R^2$ are phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)-phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl.

The radical $R^3$ is hydrogen or a $C_1$-$C_{40}$ radical. $R^3$ is preferably hydrogen or a cyclic, branched or unbranched $C_1$-$C_{20}$-, preferably $C_1$-$C_{10}$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^3$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl or 2-phenylethyl, in particular hydrogen, methyl, ethyl or isopropyl.

The radicals $R^2$ and $R^3$ may also together form a ring system which can be either monocyclic or polycyclic. The radicals $R^2$ and $R^3$ preferably together form a substituted or unsubstituted, in particular unsubstituted, 1,3-butadiene-1,4-diyl group.

The radical $R^4$ is hydrogen or a $C_1$-$C_{40}$ radical. $R^4$ is preferably hydrogen or a cyclic, branched or unbranched $C_1$-$C_{20}$-, preferably $C_1$-$C_{10}$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^4$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl and 2-phenylethyl, in particular hydrogen, methyl, ethyl or isopropyl.

The radical $R^5$ is a $C_1$-$C_{40}$ radical. $R^5$ is preferably a cyclic, branched or unbranched, preferably unbranched, $C_1$-$C_{20}$-, preferably $C_1$-$C_{10}$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^5$ are methyl, ethyl, n-propyl, n-butyl, n-pentyl, n-hexyl, n-heptyl, n-octyl, benzyl and 2-phenylethyl, in particular methyl or ethyl, very particularly preferably methyl.

The radicals $R^1$, $R^2$, $R^3$, $R^4$ and $R^5$ may, according to the present invention, also contain functional groups without changing the polymerization properties of the novel organometallic transition metal compounds of the formula (I), as long as these functional groups are chemically inert under the polymerization conditions.

Z is a divalent group $CR^8R^9$—$CR^{10}R^{11}$, where $R^8$, $R^9$, $R^{10}$ and $R^{11}$ are identical or different and are each hydrogen or a $C_1$-$C_{40}$ radical. $R^8$, $R^9$, $R^{10}$ and $R^{11}$ are preferably each hydrogen, a trimethylsilyl group, a $C_1$-$C_{10}$-, preferably $C_1$-$C_3$-alkyl group, a $C_1$-$C_{10}$-fluoroalkyl group, a $C_6$-$C_{10}$-fluoroaryl group, a $C_6$-$C_{10}$-aryl group, a $C_8$-$C_{40}$-arylalkenyl group, a $C_7$-$C_{40}$-arylalkyl group or a $C_7$-$C_{40}$-alkylaryl group. Two adjacent radicals together with the atoms connecting them may also form a saturated or unsaturated ring having from 4 to 15 carbon atoms. The radicals $R^8$, $R^9$, $R^{10}$ and $R^{11}$ are particularly preferably hydrogen.

Particularly preferred embodiments of Z are the bridges: ethylidene, 1-methylethylidene, 1,1-dimethylethylidene, 1,2-dimethylethylidene, 1,1,2,2-tetramethylethylidene, in particular ethylidene.

Furthermore, according to the present invention, the substituents are, unless restricted further, defined as follows:

The term "$C_1$-$C_{40}$ radical" as used in the present context refers to $C_1$-$C_{40}$-alkyl radicals, $C_1$-$C_{10}$-fluoroalkyl radicals, $C_1$-$C_{12}$-alkoxy radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkinyl radicals, $C_7$-$C_{40}$-arylalkyl radicals or $C_8$-$C_{40}$-arylalkenyl radicals.

The term "alkyl" as used in the present context encompasses linear or singly or multiply branched saturated hydrocarbons which may also be cyclic. Preference is given to a $C_1$-$C_{18}$-alkyl such as methyl, ethyl, n-propyl, n-butyl, n-pentyl, n-hexyl, n-heptyl, n-octyl, n-nonyl, n-decyl, cyclopentyl or cyclohexyl, isopropyl, isobutyl, isopentyl, isohexyl, sec-butyl or tert-butyl.

The term "alkenyl" as used in the present context encompasses linear or singly or multiply branched hydrocarbons having at least one C—C double bond. In the case of a plurality of C—C double bonds, these may be cumulated or may alternate.

The term "aryl" as used in the present context refers to aromatic and, possibly fused, polyaromatic hydrocarbon substituents which may be unsubstituted or monosubstituted or polysubstituted by linear or branched $C_1$-$C_{18}$-alkyl, $C_1$-$C_{18}$-alkoxy, $C_2$-$C_{10}$alkenyl or $C_3$-$C_{15}$-alkylalkenyl. Preferred examples of substituted and unsubstituted aryl radicals are, in particular, phenyl, 4-methylphenyl, 4-ethylphenyl, 4-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl and 4-trifluoromethylphenyl.

The term "heteroaromatic radical" as used in the present context refers to aromatic hydrocarbon substituents in which one or more carbon atoms are replaced by nitrogen, phosphorus, oxygen or sulfur atoms or combinations thereof. These may, like the aryl radicals, be unsubstituted or monosubstituted or polysubstituted by linear or branched $C_1$-$C_{18}$-alkyl, $C_2$-$C_{10}$-alkenyl or $C_3$-$C_{15}$-alkylalkenyl. Preferred examples are thienyl, furyl, pyrrolyl, pyridyl, pyrazolyl, imidazolyl, oxazolyl, thiazolyl, pyrimidinyl, pyrazinyl and the like, and also derivatives thereof which are substituted by methyl, ethyl, propyl, isopropyl and tert-butyl radicals.

The term "alkylalkenyl" as used in the present context encompasses linear or singly or multiply branched hydrocarbons having one or more C—C double bonds which are isolated, so that the substituent has both alkyl and alkenyl sections.

The term "arylalkyl" as used in the present context refers to aryl-containing substituents whose aryl radical is linked to the appropriate part of the molecule via an alkyl chain. Preferred examples are benzyl, substituted benzyl, phenethyl, substituted phenethyl and the like.

The terms fluoroalkyl and fluoroaryl indicate that at least one hydrogen atom, preferably a plurality of and at most all hydrogen atoms, of the respective substituent are replaced by fluorine atoms. Examples of fluorine-containing substituents which are preferred according to the present invention are trifluoromethyl, 2,2,2-trifluoroethyl, pentafluorophenyl, 4-trifluoromethylphenyl, 4-perfluorotert-butylphenyl and the like.

Preference is given to organometallic transition metal compounds of the formula (I) in which
  $M^1$ is an element of group 4 of the Periodic Table of the Elements,
  n is 2,
  $R^1$ is $C_1$-$C_{10}$-alkyl,
  $R^3$ is hydrogen or a $C_1$-$C_{10}$-alkyl radical,
  $R^4$ is hydrogen or a $C_1$-$C_{10}$alkyl radical,
  $R^5$ is a $C_1$-$C_{10}$-alkyl radical,
  Z is $CH_2$—$CH_2$ and
  the other variables are as defined in formula (I).

$M^1$ is preferably zirconium or hafnium, particularly preferably zirconium.

The radical $R^1$ is a $C_1$-$C_{10}$alkyl radical, in particular a $C_1$-$C_4$-alkyl radical, very particularly preferably a methyl radical.

The radical $R^3$ is hydrogen or a $C_1$-$C_{10}$-alkyl radical, in particular hydrogen or a $C_1$-$C_4$-alkyl radical, very particularly preferably hydrogen or a methyl radical.

The radical $R^4$ is hydrogen or a $C_1$-$C_{10}$-alkyl radical, in particular hydrogen or a $C_1$-$C_4$-alkyl radical, very particularly preferably hydrogen or a methyl radical.

The radical $R^5$ is a $C_1$-$C_{10}$-alkyl radical, in particular a $C_1$-$C_4$-alkyl radical, very particularly preferably a methyl radical.

Illustrative examples of novel organometallic transition metal compounds of the formula (I), which do not, however, restrict the invention, are:
  1,2-ethanediylbis(2,7-dimethyl-4,5-benzindenyl)zirconium dichloride,
  1,2-ethanediylbis(2,7-dimethyl-4-phenylindenyl)zirconium dichloride,
  1,2-ethanediylbis(2,5,7-trimethyl-4-phenylindenyl)zirconium dichloride,
  1,2-ethanediylbis(2,6,7-trimethyl-4-phenylindenyl)zirconium dichloride,
  1,2-ethanediylbis(2,5,6,7-tetramethyl-4-phenylindenyl) zirconium dichloride,
  1,2-ethanediylbis(2-ethyl-7-methyl-4-phenylindenyl)zirconium dichloride,
  1,2-ethanediylbis(2-ethyl-5,7-dimethyl-4-phenylindenyl) zirconium dichloride,
  1,2-ethanediylbis(2-ethyl-6,7-dimethyl-4-phenylindenyl) zirconium dichloride,
  1,2-ethanediylbis(2-ethyl-5,6,7-trimethyl-4-phenylindenyl)zirconium dichloride,
  1,2-ethanediylbis(2-n-butyl-7-methyl-4-phenylindenyl) zirconium dichloride,
  1,2-ethanediylbis(2-n-butyl-5,7-dimethyl-4-phenylindenyl)zirconium dichloride,
  1,2-ethanediylbis(2-n-butyl-6,7-dimethyl-4-phenylindenyl)zirconium dichloride,
  1,2-ethanediylbis(2-n-butyl-5,6,7-trimethyl-4-phenylindenyl)zirconium dichloride,
  1,2-ethanediylbis(2-isopropyl-7-methyl-4-phenylindenyl) zirconium dichloride,
  1,2-ethanediylbis(2-isopropyl-5,7-dimethyl-4-phenylindenyl)zirconium dichloride,
  1,2-ethanediylbis(2-isopropyl-6,7-dimethyl-4-phenylindenyl)zirconium dichloride,
  1,2-ethanediylbis(2-isopropyl-5,6,7-trimethyl-4-phenylindenyl)zirconium dichloride,
  1,2-ethanediylbis(2,7-dimethyl-4-(2-tolyl)indenyl)zirconium dichloride,
  1,2-ethanediylbis(2,5,7-trimethyl-4-(2-tolyl)indenyl)zirconium dichloride,
  1,2-ethanediylbis(2,6,7-trimethyl-4-(2-tolyl)indenyl)zirconium dichloride,
  1,2-ethanediylbis(2,5,6,7-tetramethyl-4-(2-tolyl)indenyl) zirconium dichloride,
  1,2-ethanediylbis(2-ethyl-7-methyl-4-(2-tolyl)indenyl) zirconium dichloride,
  1,2-ethanediylbis(2-ethyl-5,7-dimethyl-4-(2-tolyl)indenyl)zirconium dichloride,
  1,2-ethanediylbis(2-ethyl-6,7-dimethyl-4-(2-tolyl)indenyl)zirconium dichloride,
  1,2-ethanediylbis(2-ethyl-5,6,7-trimethyl-4-(2-tolyl)indenyl)zirconium dichloride,
  1,2-ethanediylbis(2-n-butyl-7-methyl-42-tolyl)indenyl) zirconium dichloride,
  1,2-ethanediylbis(2-n-butyl-5,7-dimethyl-4-(2-tolyl)indenyl)zirconium dichloride,
  1,2-ethanediylbis(2-n-butyl-6,7-dimethyl-4-(2-tolyl)indenyl)zirconium dichloride,
  1,2-ethanediylbis(2-n-butyl-5,6,7-trimethyl-4-(2-tolyl)indenyl)zirconium dichloride,
  1,2-ethanediylbis(2-isopropyl-7-methyl-4-(2-tolyl)indenyl)zirconium dichloride,
  1,2-ethanediylbis(2-isopropyl-5,7-dimethyl-4-2-tolyl)indenyl)zirconium dichloride,
  1,2-ethanediylbis(2-isopropyl-6,7-dimethyl-4-(2-tolyl)indenyl)zirconium dichloride,
  1,2-ethanediylbis(2-isopropyl-5,6,7-trimethyl-4-(2-tolyl) indenyl)zirconium dichloride,
  1,2-ethanediylbis(2,7dimethyl-4-(3-tolyl)indenyl)zirconium dichloride,
  1,2-ethanediylbis(2,5,7-trimethyl-4-(3-tolyl)indenyl)zirconium dichloride,
  1,2-ethanediylbis(2,6,7-trimethyl-4-(3-tolyl)indenyl)zirconium dichloride,
  1,2-ethanediylbis(2,5,6,7-tetramethyl-4-(3-tolyl)indenyl) zirconium dichloride,
  1,2-ethanediylbis(2-ethyl-7-methyl-4-(3-tolyl)indenyl) zirconium dichloride, 1,2-ethanediylbis(2-ethyl-5,7-dimethyl-4-(3-tolyl)indenyl)zirconium dichloride
1,2-ethanediylbis(2-ethyl-6,7-dimethyl-4-(3-tolyl)indenyl)zirconium dichloride,
1,2-ethanediylbis(2-ethyl-5,6,7-trimethyl-4-(3-tolyl)indenyl)zirconium dichloride,
1,2-ethanediylbis(2-n-butyl-7-methyl-4-(3-tolyl)indenyl)zirconium dichloride,
1,2-ethanediylbis(2-n-butyl-5,7-dimethyl-4-(3-tolyl)indenyl)zirconium dichloride,
1,2-ethanediylbis(2-n-butyl-6,7-dimethyl-4-(3-tolyl)indenyl)zirconium dichloride,
1,2-ethanediylbis(2-n-butyl-5,6,7-trimethyl-4-(3-tolyl)indenyl)zirconium dichloride,
1,2-ethanediylbis(2-isopropyl-7-methyl-4-(3-tolyl)indenyl)zirconium dichloride,
1,2-ethanediylbis(2-isopropyl-5,7-dimethyl-4-(3-tolyl)indenyl)zirconium dichloride,
1,2-ethanediylbis(2-isopropyl-6,7-dimethyl-4-3-tolyl)indenyl)zirconium dichloride,
1,2-ethanediylbis(2-isopropyl-5,6,7-trimethyl-4-(3-tolyl)indenyl)zirconium dichloride,
1,2-ethanediylbis(2,7-dimethyl-4-(4-tolyl)indenyl)zirconium dichloride,
1,2-ethanediylbis(2,5,7-trimethyl-4-(4-tolyl)indenyl)zirconium dichloride,
1,2-ethanediylbis(2,6,7-trimethyl-4-(4-tolyl)indenyl)zirconium dichloride,
1,2-ethanediylbis(2,5,6,7-tetramethyl-4-(4-tolyl)indenyl)zirconium dichloride,
1,2-ethanediylbis(2-ethyl-7-methyl-4-(4-tolyl)indenyl)zirconium dichloride,
1,2-ethanediylbis(2-ethyl-5,7-dimethyl-4-(4-tolyl)indenyl)zirconium dichloride,
1,2-ethanediylbis(2-ethyl-6,7-dimethyl-4-(4-tolyl)indenyl)zirconium dichloride,
1,2-ethanediylbis(2-ethyl-5,6,7-trimethyl-44-tolyl)indenyl)zirconium dichloride,
1,2-ethanediylbis(2-n-butyl-7-methyl-4-(4-tolyl)indenyl)zirconium dichloride,
1,2-ethanediylbis(2-n-butyl-5,7-dimethyl-(4-tolyl)indenyl)zirconium dichloride,
1,2-ethanediylbis(2-n-butyl6,7-dimethyl-4-4-tolyl)indenyl)zirconium dichloride,
1,2-ethanediylbis(2-n-butyl-5,6,7-trimethyl-4-(4-tolyl)indenyl)zirconium dichloride,
1,2-ethanediylbis(2-isopropyl-7-methyl-4-(4-tolyl)indenyl)zirconium dichloride,
1,2-ethanediylbis(2-isopropyl-5,7-dimethyl-4(4-tolyl)indenyl)zirconium dichloride,
1,2-ethanediylbis(2-isopropyl-6,7-dimethyl-4-(4-tolyl)indenyl)zirconium dichloride,
1,2-ethanediylbis(2-isopropyl-5,6,7-trimethyl-4-(4-tolyl)indenyl)zirconium dichloride,
1,2-ethanediylbis(2,7-dimethyl-4-(3,5-dimethylphenyl)indenyl)zirconium dichloride,
1,2-ethanediylbis(2,5,7-trimethyl-4-(3,5-dimethylphenyl)indenyl)zirconium dichloride,
1,2-ethanediylbis(2,6,7-trimethyl-4-(3,5-dimethylphenyl)indenyl)zirconium dichloride,
1,2-ethanediylbis(2,5,6,7-tetramethyl-4-(3,5-dimethylphenyl)indenyl)zirconium dichloride,
1,2-ethanediylbis(2-ethyl-7-methyl-4-(3,5-dimethylphenyl)indenyl)zirconium dichloride,
1,2-ethanediylbis(2-ethyl-5,7-dimethyl-4-(3,5-dimethylphenyl)indenyl)zirconium dichloride,
1,2-ethanediylbis(2-ethyl-6,7-dimethyl-4-(3,5-dimethylphenyl)indenyl)zirconium dichloride,
1,2-ethanediylbis(2-ethyl-5,6,7-trimethyl-4-(3,5-dimethylphenyl)indenyl)zirconium dichloride,
1,2-ethanediylbis(2-n-butyl-7-methyl-4-(3,5-dimethylphenyl)indenyl)zirconium dichloride,
1,2-ethanediylbis(2-n-butyl-5,7-dimethyl-4-(3,5-dimethylphenyl)indenyl)zirconium dichloride
1,2-ethanediylbis(2-n-butyl-6,7-dimethyl-4-(3,5-dimethylphenyl)indenyl)zirconium dichloride,
1,2-ethanediylbis(2-n-butyl-5,6,7-trimethyl-4-(3,5-dimethylphenyl)indenyl)zirconium dichloride,
1,2-ethanediylbis(2-isopropyl-7-methyl-4-(3,5-dimethylphenyl)indenyl)zirconium dichloride,
1,2-ethanediylbis(2-isopropyl-5,7-dimethyl-4-(3,5-dimethylphenyl)indenyl)zirconium dichloride,
1,2-ethanediylbis(2-isopropyl-6,7-dimethyl-4-(3, 5-dimethylphenyl)indenyl)zirconium dichloride,
1,2-ethanediylbis(2-isopropyl-5,6,7-trimethyl-4-(3,5-dimethylphenyl)indenyl)zirconium dichloride,
1,2-ethanediylbis(2,7-dimethyl-4-(3,5-di-tert-butylphenyl)indenyl)zirconium dichloride,
1,2-ethanediylbis(2,5,7-trimethyl-4-(3,5-di-tert-butylphenyl)indenyl)zirconium dichloride,
1,2-ethanediylbis(2,6,7-trimethyl-4-(3,5-di-tert-butylphenyl)indenyl)zirconium dichloride
1,2-ethanediylbis(2,5,6,7-tetramethyl-4-(3,5-di-tert-butylphenyl)indenyl)zirconium dichloride,
1,2-ethanediylbis(2-ethyl-7-methyl-4-(3,5-di-tert-butylphenyl)indenyl)zirconium dichloride,
1,2-ethanediylbis(2-ethyl-5,7-dimethyl-4-(3,5-di-tert-butylphenyl)indenyl)zirconium dichloride,
1,2-ethanediylbis(2-ethyl-6,7-dimethyl-4-(3,5-di-tert-butylphenyl)indenyl)zirconium dichloride,
1,2-ethanediylbis(2-ethyl-5,6,7-trimethyl-4-(3,5-di-tert-butylphenyl)indenyl)zirconium dichloride,
1,2-ethanediylbis(2-n-butyl-7-methyl-4-(3,5-di-tert-butylphenyl)indenyl)zirconium dichloride,
1,2-ethanediylbis(2-n-butyl-5,7-dimethyl-4-(3,5-di-tert-butylphenyl)indenyl)zirconium dichloride,
1,2-ethanediylbis(2-n-butyl-6,7-dimethyl-4-(3,5-di-tert-butylphenyl)indenyl)zirconium dichloride,
1,2-ethanediylbis(2-n-butyl-5,6,7-trimethyl-4-(3,5-di-tert-butylphenyl)indenyl)zirconium dichloride,
1,2-ethanediylbis(2-isopropyl-7-methyl-4-3,5-di-tert-butylphenyl)indenyl)zirconium dichloride,
1,2-ethanediylbis(2-isopropyl-5,7-dimethyl-4-(3,5-di-tert-butylphenyl)indenyl)zirconium dichloride,
1,2-ethanediylbis(2-isopropyl-6,7-dimethyl-4-(3,5-di-tert-butylphenyl)indenyl)zirconium dichloride,
1,2-ethanediylbis(2-isopropyl-5,6,7-trimethyl-4-(3,5-di-tert-butylphenyl)indenyl)zirconium dichloride,
1,2-ethanediylbis(2,7-dimethyl-4-p-tert-butylphenyl)indenyl)zirconium dichloride,
1,2-ethanediylbis(2,5,7-trimethyl-4-(p-tert-butylphenyl)indenyl)zirconium dichloride,
1,2-ethanediylbis(2,6,7-trimethyl-4(p-tert-butylphenyl)indenyl)zirconium dichloride,
1,2-ethanediylbis(2,5,6,7-tetramethyl-4-(p-tert-butylphenyl)indenyl)zirconium dichloride,
1,2-ethanediylbis(2-ethyl-7-methyl-4p-tert-butylphenyl)indenyl)zirconium dichloride,
1,2-ethanediylbis(2-ethyl-5,7-dimethyl-4-(p-tert-butylphenyl)indenyl)zirconium dichloride,
1,2-ethanediylbis(2-ethyl-6,7-dimethyl-4-(p-tert-butylphenyl)indenyl)zirconium dichloride, 1,2-ethanediylbis(2-ethyl-5,6,7-trimethyl-4-(p-tert-butylphenyl)indenyl)zirconium dichloride,
1,2-ethanediylbis(2-n-butyl-7-methyl-4-(p-tert-butylphenyl)indenyl)zirconium dichloride,
1,2-ethanediylbis(2-n-butyl-5,7-dimethyl-4-(p-tert-butylphenyl)indenyl)zirconium dichloride,
1,2-ethanediylbis(2-n-butyl4,7-dimethyl-4-(p-tert-butylphenyl)indenyl)zirconium dichloride,
1,2-ethanediylbis(2-n-butyl-5,6,7-trimethyl-4-(p-tert-butylphenyl)indenyl)zirconium dichloride,
1,2-ethanediylbis(2-isopropyl-7-methyl-4-(p-tert-butylphenyl)indenyl)zirconium dichloride,
1,2-ethanediylbis(2-isopropyl-5,7-dimethyl-4-(p-tert-butylphenyl)indenyl)zirconium dichloride,
1,2-ethanediylbis(2-isopropyl4,7-dimethyl-4-(p-tert-butylphenyl)indenyl)zirconium dichloride,
1,2-ethanediylbis(2-isopropyl-5,6,7-trimethyl-4-(p-tert-butylphenyl)indenyl)zirconium dichloride,
1,2-ethanediylbis(2,7-dimethyl-4-(2,3-dimethylphenyl)indenyl)zirconium dichloride,
1,2-ethanediylbis(2,5,7-trimethyl-4-(2,4-dimethylphenyl)indenyl)zirconium dichloride,
1,2-ethanediylbis(2,6,7-trimethyl-4-(2,5-dimethylphenyl)indenyl)zirconium dichloride,
1,2-ethanediylbis(2,5,6,7-tetramethyl-4-(2,6-dimethylphenyl)indenyl)zirconium dichloride,
1,2-ethanediylbis(2ethyl-7-methyl-4-(3,4-dimethylphenyl)indenyl)zirconium dichloride,
1,2-ethanediylbis(2-ethyl-5,7-dimethyl-4-(2,3-dimethylphenyl)indenyl)zirconium dichloride,
1,2-ethanediylbis(2-ethyl-6,7-dimethyl-4-(2,4-dimethylphenyl)indenyl)zirconium dichloride,
1,2-ethanediylbis(2-ethyl-5,6,7-trimethyl-4-(2,5-dimethylphenyl)indenyl)zirconium dichloride,
1,2-ethanediylbis(2-n-butyl-7-methyl-4-(2,6-dimethylphenyl)indenyl)zirconium dichloride,
1,2-ethanediylbis(2-n-butyl-5,7-dimethyl-4-(3,4-dimethylphenyl)indenyl)zirconium dichloride,
1,2-ethanediylbis(2-n-butyl-6,7-dimethyl-4-(2,3-dimethylphenyl)indenyl)zirconium dichloride,
1,2-ethanediylbis(2-n-butyl-5,6,7-trimethyl-4-(2,4-dimethylphenyl)indenyl)zirconium dichloride,
1,2-ethanediylbis(2-isopropyl-7-methyl-4-(2,5-dimethylphenyl)indenyl)zirconium dichloride,
1,2-ethanediylbis(2-isopropyl-5,7-dimethyl-4-(2,6-dimethylphenyl)indenyl)zirconium dichloride,
1,2-ethanediylbis(2-isopropyl4,7-dimethyl-4-(3,4-dimethylphenyl)indenyl)zirconium dichloride,
1,2-ethanediylbis(2-isopropyl-5,6,7-trimethyl-4-(2,3-dimethylphenyl)indenyl)zirconium dichloride,
1,2-ethanediylbis(2,7-dimethyl-4-(1-naphthyl)indenyl)zirconium dichloride,
1,2-ethanediylbis(2,5,7-trimethyl-4-(1-naphthyl)indenyl)zirconium dichloride,
1,2-ethanediylbis(2,6,7-trimethyl-4-(1-naphthyl)indenyl)zirconium dichloride,
1,2-ethanediylbis(2,5,6,7-tetramethyl-4-(1-naphthyl)indenyl)zirconium dichloride,
1,2-ethanediylbis(2-ethyl-7-methyl-4(1-naphthyl)indenyl)zirconium dichloride,
1,2-ethanediylbis(2-ethyl-5,7-dimethyl-4-(1-naphthyl)indenyl)zirconium dichloride,
1,2-ethanediylbis(2-ethyl6,7-dimethyl-4-(1-naphthyl)indenyl)zirconium dichloride,
1,2-ethanediylbis(2-ethyl-5,6,7-trimethyl-4-(1-naphthyl)indenyl)zirconium dichloride,
1,2-ethanediylbis(2-n-butyl-7-methyl-4-(1-naphthyl)indenyl)zirconium dichloride,
1,2-ethanediylbis(2-n-butyl-5,7-dimethyl-4-(1-naphthyl)indenyl)zirconium dichloride,
1,2-ethanediylbis(2-n-butyl-6,7-dimethyl-4-(1-naphthyl)indenyl)zirconium dichloride,
1,2-ethanediylbis(2-n-butyl-5,6,7-trimethyl-4-(1-naphthyl)indenyl)zirconium dichloride,
1,2-ethanediylbis(2-isopropyl-7-methyl-4-(1-naphthyl)indenyl)zirconium dichloride,
1,2-ethanediylbis(2-isopropyl-5,7-dimethyl-4-(1-naphthyl)indenyl)zirconium dichloride,
1,2-ethanediylbis(2-isopropyl4,7-dimethyl-4-(1-naphthyl)indenyl)zirconium dichloride,
1,2-ethanediylbis(2-isopropyl-5,6,7-trimethyl-4-(1-naphthyl)indenyl)zirconium dichloride,
1,2-ethanediylbis(2,7-dimethyl-4-(2-naphthyl)indenyl)zirconium dichloride,
1,2-ethanediylbis(2,5,6,7-tetramethyl-4-(2-naphthyl)indenyl)zirconium dichloride,
1,2-ethanediylbis(2-ethyl-7-methyl-4-(2-naphthyl)indenyl)zirconium dichloride, .
1,2-ethanediylbis(2-ethyl-5,6,7-trimethyl-4-(2-naphthyl)indenyl)zirconium dichloride,
1,2-ethanediylbis(2-n-butyl-7-methyl-4-(2-naphthyl)indenyl)zirconium dichloride,
1,2-ethanediylbis(2-n-butyl-5,6,7-trimethyl-4-(2-naphthyl)indenyl)zirconium dichloride,
1,2-ethanediylbis(2-isopropyl-7-methyl-4-(2-naphthyl)indenyl)zirconium dichloride,
1,2-ethanediylbis(2-isopropyl-5,6,7-trimethyl-4-(2-naphthyl)indenyl)zirconium dichloride,
1,2-ethanediylbis(2,7-dimethyl-4-(9-phenanthryl)indenyl)zirconium dichloride,
1,2-ethanediylbis(2,5,6,7-tetramethyl-4-(9-phenanthryl)indenyl)zirconium dichloride,
1,2-ethanediylbis(2-ethyl-7-methyl-4-(9-phenanthryl)indenyl)zirconium dichloride,
1,2-ethanediylbis(2-ethyl-5,6,7-trimethyl-4-(9-phenanthryl)indenyl)zirconium dichloride,
1,2-ethanediylbis(2-n-butyl-7-methyl-4-(9-phenanthryl)indenyl)zirconium dichloride,
1,2-ethanediylbis(2-n-butyl-5,6,7-trimethyl-4-(9-phenanthryl)indenyl)zirconium dichloride,
1,2-ethanediylbis(2-isopropyl-7-methyl-4-(9-phenanthryl)indenyl)zirconium dichloride,
1,2-ethanediylbis(2-isopropyl-5,6,7-trimethyl-4-(9-phenanthryl)indenyl)zirconium dichloride,
1,2-ethanediylbis(2,7-dimethyl-4-(p-trimethylsilylphenyl)indenyl)zirconium dichloride,
1,2-ethanediylbis(2,5,6,7-tetramethyl-4-(p-trimethylsilylphenyl)indenyl)zirconium dichloride,
1,2-ethanediylbis(2-ethyl-7-methyl-4-(p-trimethylsilylphenyl)indenyl)zirconium dichloride, 1,2-ethanediylbis(2-ethyl-5,6,7-trimethyl-4-(p-trimethylsilylphenyl)indenyl)zirconium dichloride,
1,2-ethanediylbis(2-n-butyl-7-methyl-4-(p-trimethylsilylphenyl)indenyl)zirconium dichloride,
1,2-ethanediylbis(2-n-butyl-5,6,7-trimethyl-4-(p-trimethylsilylphenyl)indenyl)zirconium dichloride,
1,2-ethanediylbis(2-isopropyl-7-methyl-4-(p-trimethylsilylphenyl)indenyl)zirconium dichloride,
1,2-ethanediylbis(2-isopropyl-5,6,7-trimethyl-4-(p-trimethylsilylphenyl)indenyl)zirconium dichloride,
1,2-ethanediylbis(2,7-dimethyl-4-3,5-diphenylphenyl)indenyl)zirconium dichloride,
1,2-ethanediylbis(2,5,6,7-tetramethyl-4-(3,5-diphenylphenyl)indenyl)zirconium dichloride,
1,2-ethanediylbis(2-ethyl-7-methyl-4-(3,5-diphenylphenyl)indenyl)zirconium dichloride,
1,2-ethanediylbis(2-ethyl-5,6,7-trimethyl-4-(3,5-diphenylphenyl)indenyl)zirconium dichloride,
1,2-ethanediylbis(2-n-butyl-7-methyl-4-(3,5-diphenylphenyl)indenyl)zirconium dichloride,
1,2-ethanediylbis(2-n-butyl-5,6,7-trimethyl-4-(3,5-diphenylphenyl)indenyl)zirconium dichloride,
1,2-ethanediylbis(2-isopropyl-7-methyl-4-(3,5-diphenylphenyl)indenyl)zirconium dichloride,
1,2-ethanediylbis(2-isopropyl-5,6,7-trimethyl-4-(3,5-diphenylphenyl)indenyl)zirconium dichloride,
1,2-ethanediylbis(2,7-dimethyl-4-(2,3,4-trimethylphenyl)indenyl)zirconium dichloride,
1,2-ethanediylbis(2,5,6,7-tetramethyl-4-(2,3,4-trimethylphenyl)indenyl)zirconium dichloride,
1,2-ethanediylbis(2,7-dimethyl-4-(p-sec-butylphenyl)indenyl)zirconium dichloride,
1,2-ethanediylbis(2,5,6,7-tetramethyl-4-p-sec-butylphenyl)indenyl)zirconium dichloride,
1,2-ethanediylbis(2,7-dimethyl-4-p-cyclohexylphenyl)indenyl)zirconium dichloride,
1,2-ethanediylbis(2,5,6,7-tetramethyl-4-(p-cyclohexylphenyl)indenyl)zirconium dichloride,
1,2-ethanediylbis(2,7-dimethyl-4-(p-isopropylphenyl)indenyl)zirconium dichloride,
1,2-ethanediylbis(2,5,6,7-tetramethyl-4-p-isopropylphenyl)indenyl)zirconium dichloride.
1,2-ethanediylbis(2-(2-(5-methyl)thienyl)-7-methyl-4-(3,5-diphenylphenyl)indenyl)zirconium dichloride,
1,2-ethanediylbis(2-(2-(5-methyl)furyl)-7-methyl-4-(p-tert-butylphenyl)indenyl)zirconium dichloride, In the homopolymerization of α-olefins, in particular polypropylene, the novel organometallic transition metal compounds of the formula (I) give homopolymers, in particular isotactic polypropylene, having a melting point higher than that of homopolymers prepared using the previously known metallocenes having a related substitution pattern.

The novel organometallic transition metal compounds of the formula (I) can be prepared by methods as described in WO 02/18397. In these methods, the organometallic transition metal compounds of the formula (I) are usually obtained as a mixture of diastereomers, with the racemic isomer giving highly isotactic polypropylene while the corresponding, undesired diastereomer, viz. the meso form, usually gives atactic polypropylene. The terms "meso" and "racemic" in the context of metallocenes are known and are defined, for example, in Rheingold et al. Organometallics 11 (1992), pages 1869-1876.

The organometallic transition metal compounds of the formula (I) can also be used as a mixture of diastereomers for the preparation of catalysts.

The invention further provides a biscyclopentadienyl ligand system of the formula (II)

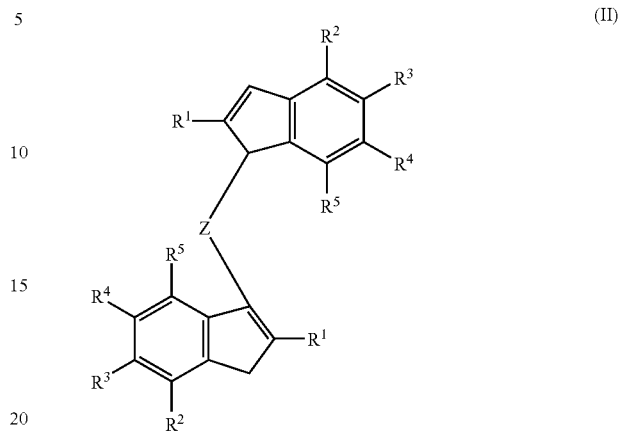

or its double bond isomers,
where the variables $R^1$, $R^2$, $R^3$, $R^4$, $R^5$ and Z are as defined in formula (I).

The double bond isomers of the compound of the formula (II) result from a formal shift of one of the double bonds in the two five-membered rings.

Particular preference is given to a biscyclopentadienyl ligand system of the formula (II) or its double bond isomer where
$R^1$ is $C_1$-$C_{10}$-alkyl,
$R^3$ is hydrogen or a $C_1$-$C_{10}$-alkyl radical,
$R^4$ is hydrogen or a $C_1$-$C_{10}$-alkyl radical,
$R^5$ is a $C_1$-$C_{10}$-alkyl radical,
Z is $CH_2$—$CH_2$ and
$R^2$ is as defined in formula (I).

The substitution pattern of the biscyclopentadienyl ligand systems of the formula (II) is decisive for the particular polymerization properties of the organometallic transition metal compounds in which these biscyclopentadienyl ligand systems are present.

The invention further provides for the use of a biscyclopentadienyl ligand system of the formula (II) for preparing an organometallic transition metal compound, preferably for preparing an organometallic transition metal compound containing an element of group 4 of the Periodic Table of the Elements, in particular zirconium.

The present invention therefore also provides a process for preparing an organometallic transition metal compound, which comprises reacting a biscyclopentadienyl ligand system of the formula (II) or a bisanion prepared therefrom with a transition metal compound. The usual procedure is firstly to doubly deprotonate a ligand system of the formula (II) by means of a base such as n-butyllithium and subsequently to react the product with a suitable transition metal source, for example zirconium tetrachloride. As an alternative, the uncharged biscyclopentadienyl ligand system of the formula (II) can also be reacted directly with a suitable transition metal source having strongly basic ligands, for example tetrakis(dimethylamino)zirconium.

The novel organometallic transition metal compounds of the formula (I) are highly active constituents of catalysts for the polymerization of olefins, particularly in the presence of suitable cocatalysts.

The present invention therefore also provides a catalyst system comprising at least one organometallic transition metal compound of the formula (I) and at least one cocatalyst.

The cocatalyst and the novel organometallic transition metal compound of the formula (I) together form a polymerization-active catalyst system in which the cocatalyst serves as cation-forming compound.

Suitable cation-forming compounds which are able to react with an organometallic transition metal compound according to the present invention to convert it into a cationic compound are, for example, compounds such as an aluminoxane, a strong uncharged Lewis acid, an ionic compound having a Lewis-acid cation or an ionic compound containing a Brönsted acid as cation. In the case of metallocene complexes as organometallic transition metal compound, the cation-forming compounds are frequently also referred to as compounds capable of forming metallocenium ions.

As aluminoxanes, it is possible to use, for example, the compounds described in WO 00/31090. Particularly useful compounds of this type are open-chain or cyclic aluminoxane compounds of the formula (III) or (IV)

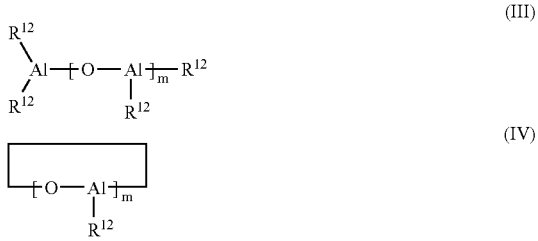

where
R$^{12}$ is a $C_1$-$C_4$-alkyl group, preferably a methyl or ethyl group, and m is an integer from 5 to 30, preferably from 10 to 25.

These oligomeric aluminoxane compounds are usually prepared by reacting a solution of trialkylaluminum with water. In general, the oligomeric aluminoxane compounds obtained in this way are in the form of mixtures of both linear and cyclic chain molecules of different lengths, so that m is to be regarded as a mean. The aluminoxane compounds can also be present in admixture with other metal alkyls, preferably aluminum alkyls.

Furthermore, modified aluminoxanes in which some of the hydrocarbon radicals or hydrogen atoms have been replaced by alkoxy, aryloxy, siloxy or amide groups can also be used in place of the aluminoxane compounds of the formula (III) or (IV).

It has been found to be advantageous to use the novel organometallic transition metal compound of the formula (I) and the aluminoxane compounds in such amounts that the atomic ratio of aluminum from the aluminoxane compounds to the transition metal from the organometallic transition metal compound is in the range from 10:1 to 1000:1, preferably in the range from 20:1 to 500:1 and in particular in the range from 30:1 to 400:1.

As strong, uncharged Lewis acids, preference is given to compounds of the formula (V)

$$M^2X^1X^2X^3 \quad (V)$$

where
M$^2$ is an element of group 13 of the Periodic Table of the Elements, in particular B, Al or Ga, preferably B, X$^1$, X$^2$ and X$^3$ are each independently of one another hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryl, preferably pentafluorophenyl.

Further examples of strong, uncharged Lewis acids are mentioned in WO 00/31090.

Particular preference is given to compounds of the formula (V) in which $X^1$, $X^2$ and $X^3$ are identical, preferably tris (pentafluorophenyl)borane.

Strong uncharged Lewis acids which are suitable as cation-forming compounds also include the reaction products from the reaction of a boronic acid with two equivalents of a trialkylaluminum or the reaction products from the reaction of a trialkylaluminum with two equivalents of an acidic fluorinated, in particular perfluorinated, carbon compound such as pentafluorophenol or bis(pentafluorophenyl)borinic acid.

Suitable ionic compounds having Lewis-acid cations include salt-like compounds of the cation of the formula (VI)

$$[(Y^{a+})Q_1Q_2\ldots Q_z]^{d+} \quad (VI)$$

where
Y is an element of groups 1 to 16 of the Periodic Table of the Elements,
$Q_1$ to $Q_z$ is a singly negatively charged group such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups,
a is an integer from 1 to 6 and
z is an integer from 0 to 5, and
d corresponds to the difference a-z, but d is greater than or equal to 1.

Particularly useful cations of this type are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane. In addition, a fourth compound which likewise reacts with the boron or aluminum compound, e.g. pentafluorophenol, may be added.

Ionic compounds containing Brönsted acids as cations likewise preferably have noncoordinating counterions. As Brönsted acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Preferred ionic compounds as cation-forming compounds are, in particular, N,N-dimethylanilinium tetrakis(pentafluorophenyl)borate, N, N-dimethylcyclohexylammonium tetrakis(pentafluorophenyl)borate or N,N-dimethylbenzylammonium tetrakis(pentafluorophenyl)borate.

It is also possible for two or more borate anions to be joined to one another, as in the dianion [(C$_6$F$_5$)$_2$B—C$_6$F$_4$—B(C$_6$F$_5$)$_2$]$^{2-}$, or the borate anion can be bound to the surface of a support particle via a bridge having a suitable functional group.

Further suitable cation-forming compounds are listed in WO 00/31090.

The amount of strong, uncharged Lewis acids, ionic compounds having Lewis-acid cations or ionic compounds containing Brönsted acids as cations is usually from 0.1 to 20 equivalents, preferably from 1 to 10 equivalents, per equivalent of the novel organometallic transition metal compound of the formula (I).

Further cation-forming compounds include boron-aluminum compounds such as di[bis(pentafluorophenyl)boroxy] methylalane. Boron-aluminum compounds of this type are disclosed, for example, in WO 99/06414.

It is also possible to use mixtures of all the abovementioned cation-forming compounds. Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Preference is given to using both the novel organometallic transition metal compound of the formula (I) and the cation-forming compounds in a solvent, preferably an aromatic hydrocarbon having from 6 to 20 carbon atoms, in particular xylenes and toluene.

The catalyst may further comprise a metal compound of the formula (VII)

(VII)

where

M$^3$ is an alkali metal, an alkaline earth metal or a metal of group 13 of the Periodic Table, i.e. boron, aluminum, gallium, indium or thallium, R$^{13}$ is hydrogen, C$_1$-C$_{10}$-alkyl, C$_6$-C$_{15}$-aryl, alkylaryl or arylalkyl each having from 1 to 10 carbon atoms in the alkyl part and from 6 to 20 carbon atoms in the aryl part, R$^{14}$ and R$^{15}$ are identical or different and are each hydrogen, halogen, C$_1$-C$_{10}$-alkyl, C$_6$-C$_{15}$-aryl, alkylaryl, arylalkyl or alkoxy each having from 1 to 10 carbon atoms in the alkyl radical and from 6 to 20 carbon atoms in the aryl radical, is an integer from 1 to 3, and s and t are integers from 0 to 2, where the sum r+s+t corresponds to the valence of M$^3$, with the metal compound of the formula (VII) usually not being identical to the cation-forming compound. It is also possible to use mixtures of various metal compounds of the formula (VII).

Among the metal compounds of the formula (VII), preference is given to those in which M$^3$ is lithium, magnesium or aluminum and R$^{14}$ and R$^{15}$ are each C$_1$-C$_{10}$-alkyl.

Particularly preferred metal compounds of the formula (VII) are n-butyllithium, n-butyl-n-octylmagnesium, n-butyl-n-heptylmagnesium, tri-n-hexylaluminum, triisobutylaluminum, triethylaluminum and trimethylaluminum and mixtures thereof.

If a metal compound of the formula (VII) is used, it is preferably present in the catalyst in such an amount that the molar ratio of M$^3$ from formula (VII) to transition metal M$^1$ from the novel organometallic transition metal compound of the formula (I) is from 800:1 to 1:1, in particular from 200:1 to 2:1.

Particular preference is given to a catalyst system comprising a novel organometallic transition metal compound of the formula (I) and at least one cocatalyst as cation-forming compound and further comprising a support.

To obtain such a supported catalyst system, the unsupported catalyst system can be reacted with a support. The order in which the support, the organometallic transition metal compound according to the invention and the cocatalyst are combined is in principle immaterial. The organometallic transition metal compound of the invention and the cocatalyst can be immobilized independently of one another or simultaneously. After the individual process steps, the solid can be washed with suitable inert solvents such as aliphatic or aromatic hydrocarbons.

As support, preference is given to using finely divided supports which can be any organic or inorganic, inert solids. In particular, the support can be a porous solid such as talc, a sheet silicate, an inorganic oxide or a finely divided polymer powder (e.g. polyolefin).

Suitable inorganic oxides may be found among the oxides of the elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium and titanium and also corresponding oxide mixtures. Further inorganic oxides which can be used alone or in combination with the abovementioned preferred oxidic supports are, for example, MgO, ZrO$_2$, TiO$_2$ or B$_2$O$_3$. A preferred mixed oxide is, for example, calcined hydrotalcite.

The support materials used preferably have a specific surface area in the range from 10 to 1000 m$^2$/g, a pore volume in the range from 0.1 to 5 ml/g and a mean particle size of from 1 to 500 µm. Preference is given to supports having a specific surface area in the range from 50 to 500 m$^2$/g, a pore volume in the range from 0.5 to 3.5 ml/g and a mean particle size in the range from 5 to 350 µm. Particular preference is given to supports having a specific surface area in the range from 200 to 400 m$^2$/g, a pore volume in the range from 0.8 to 3.0 ml/g and a mean particle size of from 10 to 100 µm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or under a blanket of inert gas (e.g. nitrogen), or the inorganic support can be calcined at from 200 to 1000° C. to generate, if appropriate, the desired structure of the solid and/or the desired OH concentration on the surface. The support can also be treated chemically using customary desiccants such as metal alkyls, preferably aluminum alkyls, chlorosilanes or SiCl$_4$ or else methylaluminoxane. Suitable treatment methods are described, for example, in WO 00/31090. The inorganic support material can also be chemically modified. For example, treatment of silica gel with (NH$_4$)$_2$SiF$_6$ leads to fluorination of the silica gel surface and treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and should preferably likewise be freed of adhering moisture, solvent residues or other impurities by appropriate purification and drying operations prior to use. It is also possible to use functionalized polymer supports, e.g. supports based on polystyrenes, via whose functional groups, for example ammonium or hydroxy groups, at least one of the catalyst components can be immobilized.

In a preferred embodiment of the preparation of the supported catalyst system, at least one of the novel organometallic transition metal compounds of the formula (I) is brought into contact with at least one cocatalyst as cation-forming compound in a suitable solvent, preferably giving a soluble reaction product, an adduct or a mixture.

The preparation obtained in this way is then mixed with the dehydrated or passivated support material, the solvent is removed and the resulting supported organometallic transition metal compound catalyst system is dried to ensure that all or most of the solvent is removed from the pores of the support material. The supported catalyst is obtained as a free-flowing powder. Examples of the industrial implementation of the above process are described in WO 96/00243, WO 98/40419 or WO 00/05277.

In a further preferred embodiment, the cation-forming compound is firstly applied to the support component and this supported cation-forming compound is subsequently brought into contact with the organometallic transition metal compound of the present invention.

Cocatalyst systems of importance therefore likewise include combinations obtained by combining the following components:
- 1st component: at least one defined boron or aluminum compound,
- 2nd component: at least one uncharged compound which possesses at least one acidic hydrogen atom,
- 3rd component: at least one support, preferably an inorganic oxidic support, and optionally as
- 4th component: a base, preferably an organic nitrogen-containing base, for example an amine, an aniline derivative or a nitrogen heterocycle.

The boron or aluminum compound used in the preparation of these supported cocatalysts are preferably compounds of the formula (VIII)

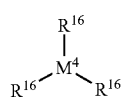
(VIII)

where
$R^{16}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{20}$-arylalkyl, $C_7$-$C_{40}$-haloarylalkyl, $C_7$-$C_{40}$-alkylaryl, $C_7$-$C_{40}$-haloalkylaryl or an $OSiR^{17}{}_3$ group, where
$R^{17}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, preferably hydrogen, $C_1$-$C_8$-alkyl or $C_7$-$C_{20}$-arylalkyl, and
$M^4$ is boron or aluminum, preferably aluminum.

Particularly preferred compounds of the formula (VIII) are trimethylaluminum, triethylaluminum and triisobutylaluminum.

The uncharged compounds which have at least one acidic hydrogen atom and can react with compounds of the formula (VIII) are preferably compounds of the formula (IX), (X) or (XI),

(IX)

(X)

(XI)

where
$R^{18}$ are identical or different and are each hydrogen, halogen, a boron-free $C_1$-$C_{40}$ group such as $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, an $Si(R^{20})_3$ group or a $CH(SiR^{20}{}_3)_2$ group, where
$R^{20}$ is a boron-free $C_1$-$C_{40}$ group such as $C_1$-$C_2$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, and
$R^{19}$ is a divalent $C_1$-$C_{40}$ group such as $C_1$-$C_2$-alkylene, $C_1$-$C_{20}$-haloalkylene, $C_6$-$C_{20}$-arylene, $C_6$-$C_{20}$-haloarylene, $C_7$-$C_{40}$-arylalkylene, $C_7$-$C_{40}$-haloaryoalkylene, $C_7$-$C_{40}$-alkylarylene, $C_7$-$C_{40}$-haloalkylarylene,
D is an element of group 16 of the Periodic Table of the Elements or an $NR^{21}$ group, where $R^{21}$ is hydrogen or a $C_1$-$C_{20}$-hydrocarbon radical such as $C_1$-$C_{20}$-alkyl or $C_6$-$C_{20}$-aryl, preferably oxygen, and
h is 1 or 2.

Suitable compounds of the formula (IX) are water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4,4',5,5',6,6'-nonafluorobiphenyl. Suitable compounds of the formula (X) include boronic acids and borinic acids, in particular borinic acids bearing perfluorinated aryl radicals, for example $(C_6F_5)_2BOH$. Suitable compounds of the formula (XI) include dihydroxy compounds in which the divalent carbon-containing group is preferably halogenated, in particular perfluorinated. An example of such a compound is 4,4'-dihydroxy-2,2',3,3',5,5',6,6'-octafluorobiphenyl hydrate.

Examples of combinations of compounds of the formula (VIII) with compounds of the formula (IX) or (XI) are trimethylaluminum/pentafluorophenol, trimethylaluminum/1-bis(pentafluorophenyl)methanol, trimethylaluminum/4-hydroxy-2,2',3,3',4,4',5,5',6,6'-nonafluorobiphenyl, triethylaluminum/pentafluorophenol and triisobutyl-aluminum/pentafluorophenol and triethylaluminum/4,4'-dihydroxy-2,2',3,3',5,5',6,6'-octafluorobiphenyl hydrate, with, for example, reaction products of the following type being able to be formed.

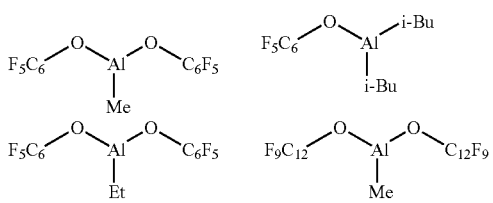

Examples of reaction products from the reaction of at least one compound of the formula (VIII) with at least one compound of the formula (X) are:

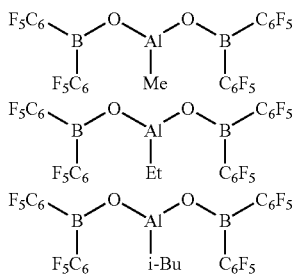

The order in which the components are combined is in principle immaterial.

If desired, the reaction products from the reaction of at least one compound of the formula (VIII) with at least one compound of the formula (IX), (X) or (XI) and optionally the organic nitrogen base are additionally combined with an organometallic compound of the formula (III), (IV), (V) and/or (VII) in order to then form the supported cocatalyst system on being combined with the support.

In a preferred embodiment, the 1st component, e.g. compounds of the formula (VIII), and the 2nd component, e.g. compounds of the formula (IX), (X) or (XI), and also a support as 3rd component and a base as 4th component are combined separately and subsequently reacted with one another, with the reaction preferably taking place in an inert solvent or suspension medium. The supported cocatalyst formed can be freed of the inert solvent or suspension medium before it is reacted with the novel organometallic transition metal compound of the formula (I) and, if desired, a metal compound of the formula (VII) to form the catalyst system.

It is also possible firstly to prepolymerize the catalyst solid with α-olefins, preferably linear $C_2$-$C_{10}$-1-alkenes, and in particular ethylene or propylene, and then to use the resulting prepolymerized catalyst solid in the actual polymerization. The mass ratio of catalyst solid used in the prepolymerization to monomer polymerized onto it is usually in the range from 1:0.1 to 1:200.

Furthermore, a small amount of an olefin, preferably a α-olefin, for example vinylcyclohexane, styrene or phenyldimethylvinylsilane, as modifying component, an antistatic or a suitable inert compound such as a wax or oil can be added as additive during or after the preparation of the supported catalyst system. The molar ratio of additives to organometallic transition metal compound according to the present invention is usually from 1:1000 to 1000:1, preferably from 1:5 to 20:1.

The present invention also provides a process for preparing polyolefins by polymerization, i.e. homopolymerization or copolymerization, of at least one olefin in the presence of a catalyst system comprising at least one of the novel organometallic transition metal compounds of the formula (I).

In general, the catalyst system is used together with a further metal compound of the formula (VII), which may be different from the metal compound or compounds of the formula (VII) used in the preparation of the catalyst system, for the polymerization or copolymerization of olefins. The further metal compound is generally added to the monomer or the suspension medium and serves to free the monomer of substances which can adversely affect the catalyst activity. It is also possible for one or more additional cation-forming compounds to be added to the catalyst system in the polymerization process.

The olefins can be functionalized, olefinic unsaturated compounds such as esters or amide derivatives of acrylic or methacrylic acid, for example acrylates, methacrylates or acrylonitrile, or be nonpolar olefinic compounds, including aryl-substituted α-olefins.

Preference is given to polymerizing olefins of the formula $R'''$—CH═CH═$R''$, where $R'''$ and $R''$ are identical or different and are each hydrogen or a carbon-containing radical having from 1 to 20 carbon atoms, in particular from 1 to 10 carbon atoms, or $R'''$ and $R''$ together with the atoms connecting them can form one or more rings.

Examples of such olefins are 1-olefins having from 2 to 40, preferably from 2 to 10, carbon atoms, e.g. ethylene, propylene, 1-butene, 1-pentene, 1-hexene, 1-heptene, 1-octene, 1-decene or 4-methyl-1-pentene or unsubstituted or substituted vinylaromatic compounds such as styrene and styrene derivatives, or dienes such as 1,3-butadiene, 1,4-hexadiene, 1,7-octadiene, 5-ethylidene-2-norbornene, norbornadiene, ethylnorbornadiene or cyclic olefins such as norbornene, tetracyclododecene or methylnorbornene.

The catalyst system of the present invention is particularly preferably used for homopolymerizing propylene or ethylene or copolymerizing ethylene with $C_3$-$C_8$-α-olefins such as propylene, 1-butene, 1-pentene, 1-hexene and/or 1-octene and/or cyclic olefins such as norbornene and/or dienes having from 4 to 20 carbon atoms, e.g. 1,4-hexadiene, norbornadiene, ethylidene-norbornene or ethylnorbornadiene or, particularly preferably, copolymerizing propylene with ethylene and/or 1-butene. Examples of copolymers obtained in this way are propylene-ethylene, propylene-1-butene, ethylene-1-butene, ethylene-1-hexene and ethylene-1-octene copolymers, and ethylene-propylene-ethylidenenorbornene and ethylene-propylene-1,4-hexadiene terpolymers.

The polymerization can be carried out in a known manner in bulk, in suspension, in the gas phase or in a supercritical medium in the customary reactors used for the polymerization of olefins. It can be carried out batchwise or preferably continuously in one or more stages. Solution processes, suspension processes, stirred gas-phase processes or gas-phase fluidized-bed processes are all possible. As solvent or suspension medium, it is possible to use inert hydrocarbons, for example isobutane, or else the monomers themselves.

The polymerization can be carried out at from −60 to 300° C. and pressures in the range from 0.5 to 3000 bar. Preference is given to temperatures in the range from 50 to 200° C., in particular from 60 to 100° C. and pressures in the range from 5 to 100 bar, in particular from 15 to 70 bar. The mean residence times are usually from 0.5 to 5 hours, preferably from 0.5 to 3 hours. Hydrogen can be used in the polymerization as molar mass regulator and/or to increase the activity. It is also possible to use customary additives such as antistatics. The catalyst system of the present invention can be used directly for the polymerization, i.e. it is introduced in pure form into the polymerization system, or it is admixed with inert components such as paraffins, oils or waxes in order to improve the meterability.

The novel organometallic transition metal compounds of the formula (I) and the catalyst systems in which they are present are especially useful for preparing propylene homopolymers having high melting points.

The polymers prepared by the process of the present invention are, in particular, suitable for producing strong, hard and stiff shaped bodies such as fibers, filaments, injection-molded parts, films, sheets or large hollow bodies (e.g. pipes).

The invention is illustrated by the following examples which do not, however, restrict the invention.

EXAMPLES

General

The preparation and handling of the organometallic compounds and their use as catalyst components were carried out in the absence of air and moisture under argon (Schienk technique or glove box). All solvents required were purged with argon and dried over molecular sieves before use.

Determination of the Melting Point:

The melting point $T_m$ was determined by means of DSC measurement in accordance with ISO standard 3146 in a first heating phase at a heating rate of 20° C. per minute to 200° C., a dynamic crystallization at a cooling rate of 20° C. per minute to 25° C. and a second heating phase at a heating rate of 20° C. per minute to 200° C. once again. The melting point was then the temperature at which the curves of the enthalpy versus the temperature measured in the second heating phase displayed a maximum.

Gel Permeation Chromatography:

Gel permeation chromatography (GPC) was carried out at 145° C. in 1,2,4-trichlorobenzene using a Waters 150C GPC apparatus. The data were evaluated using the software Win-GPC from HS-Entwicklungsgesellschaft für wissenschaftliche Hard- und Software mbH, Ober-Hilbersheim. The columns were calibrated by means of polypropylene standards having molar masses of from 100 to $10^7$ g/mol. The mass average ($M_w$) and number average ($M_n$) of the molar masses of the polymers were determined. The Q value is the ratio of mass average ($M_w$) to number average ($M_n$).

Example 1

Preparation of 1,2-ethanediylbis(2,7-dimethyl-4-(4'-tert-butylphenyl)indenyl)zirconium dichloride (1)

a) Preparation of 2-chloro-5-methylpropiophenone (1a)

43.8 9 (329 mmol) of aluminum chloride and 34.66 g (274 mmol) of 4-chlorotoluene were placed in a reaction vessel and admixed with 26.6 g (287 mmol) of propionyl chloride. Moderate HCl gas evolution occurred. The reaction mixture was stirred at 50° C. for four hours and was subsequently poured into a mixture of 350 ml of ice water and 35 ml of concentrated hydrochloric acid. The aqueous phase was extracted twice with 200 ml each time of methylene chloride. The combined organic phases were washed with 200 ml of water, 200 ml of NaHCO$_3$ solution and NaCl solution and dried over MgSO$_4$. Removal of the solvent and drying in an oil pump vacuum gave 47.06 g of (1a).

$^1$H-NMR (400 MHz, CDCl$_3$): 7.60-7.10 (m, 3H, arom-H), 2.94 (m, 2H, CH$_2$—H), 2.32 (s, 3H, CH$_3$), 1.18 (t, 3H, CH$_3$).

b) Preparation of 2-chloro-5-methylmethacrylophenone (1b)

47.0 g (257 mmol) of 2-chloro-7-methylpropiophenone (1a) and 21.2 ml (765 mmol) of aqueous formaldehyde solution were placed in a reaction vessel and a solution of 10.3 9 (257 mmol) of NaOH in 515 ml of water was added over a period of 30 minutes. The reaction mixture was stirred vigorously at 40° C. for two hours. The phases were subsequently separated and the aqueous phase was extracted twice with 200 ml of methylene chloride. The combined organic phases were washed with 200 ml of dilute hydrochloric acid and subsequently dried over MgSO$_4$. Removal of the solvent and drying in an oil pump vacuum gave 47.37 g of (1b).

$^1$H-NMR (400 MHz, CDCl$_3$): 7.39-7.05 (m, 3H, arom-H), 5.97; 5.57 (dd, 2H, CH$_2$—H), 2.31 (s, 3H, CH$_3$), 2.02 (s, 3H, CH$_3$).

c) Preparation of 7-chloro-2,4-methyl-1-indanone (1c)

349 g of concentrated sulfuric acid were placed in a reaction vessel at 65° C. and 47.3 g (243 mmol) of 2-chloro-5-methylmethacrylophenone (1b) were added dropwise over a period of two hours, the mixture was stirred at 65° C. for another 30 minutes and was then cooled to room temperature. The reaction mixture was poured into 800 g of ice water. The brownish green suspension formed was extracted three times with 300 ml each time of diethyl ether. The combined organic phases were washed with 300 ml of NaHCO$_3$ solution, 300 ml of water and 300 ml of saturated NaCl solution and subsequently dried over MgSO$_4$. Removal of the solvent and drying in an oil pump vacuum gave 39.29 g of (1c).

$^1$H-NMR (400 MHz, CDCl$_3$): 7.50-7.00 (m, 2H, arom-H), 3.32, 3.21 (dd, 2H, CH$_2$—H), 2.70 (m, 1H, CH—H), 2.28 (s, 3H, CH$_3$), 1.30 (d, 3H, CH$_3$).

d) Preparation of 2,4-dimethyl-7-(4'-tert-butylphenyl)-1-indanone (1d)

13.4 g (68.8 mmol) of 7-chloro-2,4-dimethyl-1-indanone (1c), 14.71 g (82.6 mmol) of 4-tert-butylphenylboronic acid, 16.05 g (151 mmol) of sodium carbonate, 188 ml of ethylene glycol and 30.7 ml of water were placed in a reaction vessel under a protective gas atmosphere and the mixture was heated to 80° C. While stirring vigorously, a freshly prepared catalyst solution comprising 77 mg (0.343 mmol) of palladium acetate and 1.7 ml (1.01 mmol) of an aqueous TPPTS solution (0.6 molar) in 25 ml of water was added to the reaction components and the reaction mixture was refluxed for 3 hours until the reaction was complete. After cooling to room temperature, the ethylene glycol phase was extracted three times with a total of 900 ml of toluene. The combined toluene phases were washed twice with a total of 250 ml of sodium chloride solution and dried over 150 g of sodium sulfate. Removal of the solvent and drying of the residue and subsequent distillation in an oil pump vacuum gave 18.59 g of (1d).

$^1$H-NMR (400 MHz, CDCl$_3$): 7.39-7.19 (m, 6H, arom-H), 3.30 (dd, 1H, CH$_2$—H), 2.68 (m, 1H, CH—H), 2.60 (dd, 1H, CH$_2$—H), 2.35 (s, 3H, CH$_3$), 1.34 (s, 9H, tert-butyl-H), 1.27 (d, 3H, CH$_3$).

e) Preparation of 2,7-dimethyl-4-(4'-tert-butylphenyl)indene (1e)

2.09 g (55.3 mmol) of sodium borohydride and 18.59 g (55.3 mmol) of 2,4-dimethyl-7-4'-tert-butylphenyl)-1-indanone (1d) together with 51 ml of toluene were placed in a reaction vessel. At 50° C., 9.8 ml of methanol were slowly added and the reaction mixture was stirred at 50° C. for 3 hours. After cooling to room temperature, 35 ml of 2N sulfuric acid were added and the mixture was stirred for 30 minutes. After phase separation, the organic phase was washed twice with a total of 60 ml of 2N sulfuric acid, most of the solvent was removed and the residue was taken up in 200 ml of toluene and admixed with 0.2 g of p-toluenesulfonic acid. Water was distilled off from this reaction mixture with the aid of a water separator by refluxing for 1.5 hours until the reaction was complete. The reaction mixture was washed once with 100 ml of saturated sodium hydrogen carbonate solution and dried over magnesium sulfate. After removal of the solvent, the residue was dried in an oil pump vacuum. This gave 16.8 g of the desired product (1e).

$^1$H-NMR (400 MHz, CDCl$_3$): 7.50-6.97 (m, 6H, arom-H), 6.70 (s, 1H, olefin-H), 3.24 (s, 2H, CH$_2$—H), 2.35 (s, 3H, CH$_3$), 2.15 (s, 3H, CH$_3$), 1.36 (s, 9H, tert-butyl-H).

f) Preparation of 1,2-bis(2.7-dimethyl-4-(4'-tert-butylphenyl)-1-indenyl)ethane (1f)

5.4 g (19.54 mmol, 92%-pure by GC) of 2,7-dimethyl-4-(4'-tert-butylphenyl)indene (1e) together with 25 ml of tetrahydrofuran (THF) were placed in a reaction vessel and admixed at 0° C. with 7.8 ml of an n-butyllithium solution (2.5 M in toluene), resulting in the temperature rising to 10° C. The reaction mixture was stirred at room temperature for one hour and was subsequently added dropwise to a solution of 3.0 g (9.3 mmol) of 1,2-bis(trifluoromethylsulfonyloxy)ethane in 3.5 ml of THF at −40° C. The reaction mixture obtained was stirred at −20° C. for one hour and was subsequently stirred overnight at room temperature. The solvent was then removed under reduced pressure and the residue was taken up in 100 ml of toluene. The organic phase was washed firstly with 50 ml of a 2N sodium hydroxide solution and then four times with 50 ml each time of water. The organic phase was dried over sodium sulfate and the solvent was removed under reduced pressure. This gave 7.4 g of crude product which was purified by column chromatography on silica gel, giving a clean fraction of the product (1f) in a yield of 1.9 g.

GC-MS $M^+$=578 g) Preparation of 1,2-ethanediylbis(2,7-dimethyl-4-(4'-tert-butylphenyl)indenyl)zirconium dichloride (1)

1.8 g (3.1 mmol) of ligand (1f) together with 18 ml of diethyl ether were placed in a reaction vessel and admixed at 0° C. with 4.2 ml of a solution of tert-butyllithium in pentane (1.5 M in pentane). A further 10 ml of diethyl ether were added to the yellow suspension formed and the suspension was stirred overnight at room temperature. At 0° C., 1.10 g (3.42 mmol) of zirconium tetrachloride-dimethoxyethane complex were added. After warming to room temperature, 10 ml of diethyl ether were added and the reaction mixture was stirred at room temperature for 8 hours. The solvent was removed completely under reduced pressure and the residue, viz. 2.5 g of crude complex, was admixed with 150 ml of toluene at 80° C. After filtration through a layer of Celite, the toluene solution was evaporated to about 8 ml and admixed with 5 ml of n-heptane. A solid precipitated at −30° C. and this was filtered off, analyzed by NMR and then discarded. The filtrate was once again evaporated completely, dissolved in 30 ml of toluene/5 ml of heptane at 100° C. and an insoluble residue was filtered off once again. The clear filtrate was evaporated to about 15 ml, admixed with 10 ml of heptane and stored at −30° C. for one day. The crystals which had precipitated were filtered off via a G3 frit, washed with 1 ml of heptane and dried under reduced pressure. This gave 0.2 g of the complex (1).

$^1$H-NMR (400 MHz, CDCl$_3$): 1.30, 1.32 (18H, t-Bu—H), 2.19 (6H, Me—H), 2.34 (6H, Me—H), 3.7, 4.1 (2×4H), 6.6 (2H), 6.9-7.8 (12H, aromat. H)

Example 2

0.206 mmol of 1,2-Et(2,7-Me$_2$-4-(p-$^t$Bu—Ph)-1-Ind)$_2$ZrCl$_2$ (1) from example 1 were added at room temperature to 4.33 mmol of MAO (30% strength by weight solution in toluene, manufactured by Albemarle). The solution was allowed to stand overnight at room temperature and was subsequently diluted with 10.9 ml of toluene. The diluted solution was carefully added to 10 g of silica (Sylopol 948 calcined at 600° C., manufactured by Grace). Particular attention was paid to ensuring that the colored solution was distributed uniformly over the support material. After 10 minutes, most of the solvent was removed from the catalyst suspension in an oil pump vacuum. The free-flowing catalyst powder obtained was dried in an oil pump vacuum until the volatiles content of the catalyst solid had been reduced to below 5% by weight Comparative Example A Example 2 was repeated, but 1,2-Et(2-Me-4-(p-$^t$Bu—Ph)-1-Ind)$_2$ZrCl$_2$ was used in place of the metallocene from example 1 for preparing the catalyst in this experiment.

Comparative Example B

Example 2 was repeated, but 1,2-Et(2,4,7-Me$_3$-1-Ind)$_2$ZrCl$_2$ was used in place of the metallocene from example 1 for preparing the catalyst in this experiment.

Example 3

Homopolymerization of Propene

The homopolymerization was carried out in a 5 l reactor charged with 3 l of liquid propene. The reactor had been made inert by means of nitrogen before being charged. 2.4 ml of a 20% strength by weight solution of triethylaluminum in Exsol (from Witco) were added to the propene in the reactor and the mixture was stirred at 30° C. for 15 minutes. A suspension of 500 mg of the catalyst prepared in example 2 in 20 ml of Exsol was introduced into the reactor. The reactor temperature was increased to 65° C. and the reactor was maintained at this temperature for 60 minutes. The polymerization was stopped by venting the reactor. The polymer was dried overnight under reduced pressure. The results of the polymerization and the results of the analysis of the polymer are shown in the table below.

Comparative Example C

Homopolymerization of Propene

The homopolymerization was carried out in a 2 l reactor charged with 1.5 l of liquid propene. The reactor had been made inert by means of nitrogen before being charged. 1.7 ml of a 20% strength by weight solution of triethylaluminum in Exsol (from Witco) were introduced into the reactor and the mixture was stirred at 30° C. for 15 minutes. A suspension of 600 mg of the catalyst prepared in comparative example A in 20 ml of Exsol was introduced into the reactor. The reactor temperature was increased to 65° C. and the reactor was maintained at this temperature for 60 minutes. The polymerization was stopped by venting the reactor. The polymer was dried overnight under reduced pressure.

Comparative Example D

Homopolymerization of Propene

The polymerization of comparative example C was repeated, but 930 mg of the catalyst prepared in comparative example B were used as catalyst in this experiment.

TABLE

Polymerization results and results of the analysis of the polymers

|  | Activity [kg/g*h] | $M_w$ [g/mol] | $M_w/M_n$ | $T_m$ [° C.] |
|---|---|---|---|---|
| Example 3 | 0.82 | 335 900 | 3.0 | 156.4 |
| Comparative example C | 0.40 | 315 100 | 4.2 | 153.7 |
| Comparative example D | 0.27 | 400 000 | 2.7 | 153.9 |

Units and abbreviations:
melting point ($T_m$): ° C.;
weight average molar mass ($M_w$): g/mol;
polydispersity: $Q = M_w/M_n$;
activity: mass of polymer/(mass of catalyst * polymerization time in hours)

The invention claimed is:

1. An organometallic transition metal compound of the formula (I)

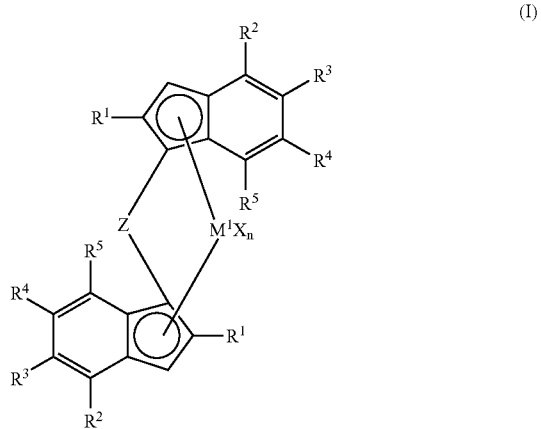

(I)

where
M¹ is an element of group 3, 4, 5 or 6 of the Periodic Table of the Elements or the lanthanides,
X are identical or different and are each halogen, hydrogen, $C_1$-$C_{20}$-alkyl, $C_2$-$C_{20}$-alkenyl, $C_6$-$C_{22}$-aryl, alkylaryl or arylalkyl each having from 1 to 10 carbon atoms in the alkyl part and from 6 to 22 carbon atoms in the aryl part, —$OR^6$ or —$NR^6R^7$, where two radicals X may also be joined to one another,
n is a natural number from 1 to 4 which corresponds to the oxidation number of M¹ minus 2,
R¹ is hydrogen or a cyclic, branched or unbranched $C_1$-$C_{20}$-alkyl radical; a $C_2$-$C_{20}$-alkenyl radical, an arylalkyl radical having from 1 to 10 carbon atoms in the alkyl part and from 6 to 22 carbon atoms in the aryl part or a $C_4$-$C_{24}$ heteroaromatic radical selected from the group consisting of substituted or unsubstituted thienyl radicals or of substituted or unsubstituted furyl radicals,
R² is a substituted or unsubstituted $C_6$-$C_{40}$-aryl radical,
R³ is hydrogen or a cyclic, branched or unbranched $C_1$-$C_{20}$-alkyl radical, $C_2$-$C_{20}$-alkenyl radical, an arylalkyl radical having from 1 to 10 carbon atoms in the alkyl part and from 6 to 22 carbon atoms in the aryl part, or the radicals R² and R³ together form a ring system,
R⁴ is hydrogen or a cyclic, branched or unbranched $C_1$-$C_{20}$-alkyl radical, a $C_2$-$C_{20}$-alkenyl radical, an arylalkyl radical having from 1 to 10 carbon atoms in the alkyl part and from 6 to 22 carbon atoms in the aryl part, R⁵ is a cyclic, branched or unbranched $C_1$-$C_{20}$-alkyl radical, a $C_2$-$C_{20}$-alkenyl radical, an arylalkyl radical having from 1 to 10 carbon atoms in the alkyl part and from 6 to 22 carbon atoms in the aryl part, and
Z is a divalent group $CR^8R^9$—$CR^{10}R^{11}$, where $R^8$, $R^9$, $R^{10}$, and $R^{11}$ are identical or different and are each hydrogen or a trimethylsilyl group, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_8$-$C_{40}$-arylalkenyl group, a $C_7$-$C_{40}$-arylalkyl group or a $C_7$-$C_{40}$-alkylaryl group or two adjacent radicals together with the atoms connecting them may form a saturated or unsaturated ring having from 4 to 15 carbon atoms.

2. An organometallic transition metal compound of the formula (I) as claimed in claim 1,
where
M¹ is an element of group 4 of the Periodic Table of the Elements,
n is 2,
R¹ is $C_1$-$C_{10}$-alkyl,
R³ is hydrogen or a $C_1$-$C_{10}$-alkyl radical,
R⁴ is hydrogen or a $C_1$-$C_{10}$-alkyl radical,
R⁵ is a $C_1$-$C_{10}$-alkyl radical and
Z is $CH_2$—$CH_2$.

3. A catalyst system for the polymerization of olefins comprising at least one organometallic transition metal compound as claimed in claim 1 and at least one cocatalyst as cation-forming compound.

4. A catalyst system as claimed in claim 3 which further comprises a support.

5. A process for preparing polyolefins by polymerization or copolymerization of at least one olefin in the presence of a catalyst system as claimed in claim 3.

6. A catalyst system as claimed in claim 3 further comprise a metal compound of the formula (VII)

(VII)

wherein
$M_3$ is an alkali metal, an alkaline earth metal or a metal of group 13 of the Periodic Table,
$R^{13}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part,
$R^{14}$ and $R^{15}$ are identical or different and are each hydrogen, halogen, $C_1$-$C_{10}$-alkyl, $C_6$-$C_{15}$-aryl, alkylaryl, arylalkyl or alkoxy each having from to 10 carbon atoms in the alkyl radical and from 6 to 20 carbon atoms in the aryl radical,
r is an integer from 1 to 3,
and
s and t are integers from 0 to 2, where the sum r+s+t corresponds to the valence of $M^3$.

7. A catalyst system as claimed in claim 6 wherein $M^3$ is boron, aluminum, gallium, indium or thallium.

8. A process for preparing an organometallic transition metal compound, which comprises reacting a biscyclopentadienyl ligand system or a bisanion prepared therefrom with a transition metal compound, the biscyclopentadienyl ligand system comprising a compound of formula (II):

9. A biscyclopentadienyl ligand system of formula (II):

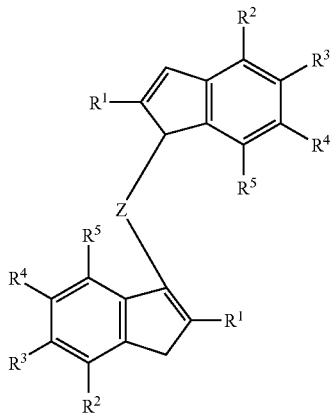
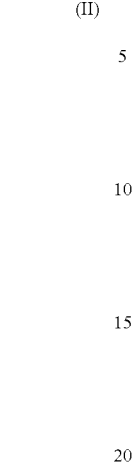

(II)

or its double bond isomers,
where

- $R^1$ is hydrogen or a cyclic, branched or unbranched $C_1$-$C_{20}$-alkyl radical, a $C_2$-$C_{20}$-alkenyl radical, an arylalkyl radical having from 1 to 10 carbon atoms in the alkyl part and from 6 to 22 carbon atoms in the aryl part or a $C_4$-$C_{24}$-heteroaromatic radical selected from the group consisting of substituted or unsubstituted thienyl radicals or of substituted or unsubstituted furyl radicals,
- $R^2$ is a substituted or unsubstituted $C_6$-$C_{40}$-aryl radical,
- $R^3$ is hydrogen or a cyclic, branched or unbranched $C_1$-$C_{20}$-alkyl radical, $C_2$-$C_{20}$-alkenyl radical, an arylalkyl radical having from 1 to 10 carbon atoms in the alkyl part and from 6 to 22 carbon atoms in the aryl part, or the radicals $R^2$ and $R^3$ together form a ring system,
- $R^4$ is hydrogen or a cyclic, branched or unbranched $C_1$-$C_{20}$-alkyl radical, a $C_2$-$C_{20}$-alkenyl radical, an arylalkyl radical having from 1 to 10 carbon atoms in the alkyl part and from 6 to 22 carbon atoms in the aryl part,
- $R^5$ is a cyclic, branched or unbranched $C_1$-$C_{20}$-alkyl radical, a $C_2$-$C_{20}$-alkenyl radical, an arylalkyl radical having from 1 to 10 carbon atoms in the alkyl part and from 6 to 22 carbon atoms in the aryl part, and
- Z is a divalent group $CR^8R^9$—$CR^{10}R^{11}$, where $R^8$, $R^9$, $R^{10}$ and $R^{11}$ are identical or different and are each hydrogen or a trimethylsilyl group, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_8$-$C_{40}$-arylalkenyl group, a $C_7$-$C_{40}$-arylalkyl group or a $C_7$-$C_{40}$-alkylaryl group or two adjacent radicals together with the atoms connecting them form a saturated or unsaturated ring having from 4 to 15 carbon atoms.

* * * * *

UNITED STATES PATENT AND TRADEMARK OFFICE
CERTIFICATE OF CORRECTION

| | | |
|---|---|---|
| PATENT NO. | : 7,405,261 B2 | Page 1 of 1 |
| APPLICATION NO. | : 10/537677 | |
| DATED | : July 29, 2008 | |
| INVENTOR(S) | : Jörg Schulte et al. | |

It is certified that error appears in the above-identified patent and that said Letters Patent is hereby corrected as shown below:

At col. 27, line 48, delete "$R_{10}$" and insert instead --$R^{10}$-- (per Amendment, claim 9, page 5, line 15, dated 6/21/07).

Signed and Sealed this

Tenth Day of November, 2009

David J. Kappos
*Director of the United States Patent and Trademark Office*